US005747600A

United States Patent [19]

Fang

[11] Patent Number: 5,747,600
[45] Date of Patent: May 5, 1998

[54] RECONSTITUTABLE POLYACRYLAMIDE MATERIALS AND METHODS FOR PRODUCING SAME

[76] Inventor: Ta-Yun Fang, 13755 N.W. Burton St., Portland, Oreg. 97229

[21] Appl. No.: 551,551

[22] Filed: Nov. 1, 1995

Related U.S. Application Data

[63] Continuation of Ser. No. 267,147, Jun. 24, 1994, abandoned.

[51] Int. Cl.[6] .............................. C08L 20/56; C08J 3/075; C08K 5/15; C08K 5/05
[52] U.S. Cl. .................. 525/329.4; 524/56; 524/386; 524/388; 526/934; 528/480
[58] Field of Search .......................... 524/56, 386, 388; 525/329.4; 528/480; 526/934

[56] References Cited

U.S. PATENT DOCUMENTS

| | | | |
|---|---|---|---|
| 4,048,377 | 9/1977 | Boschetti et al. | 524/56 |
| 4,699,705 | 10/1987 | Ogawa et al. | 204/299 R |
| 4,746,551 | 5/1988 | Allen et al. | 204/182.8 |
| 5,145,676 | 9/1992 | Fahey, III et al. | 424/85.1 |
| 5,159,049 | 10/1992 | Allen | 524/56 |
| 5,397,449 | 3/1995 | Zewert et al. | 204/182.8 |

OTHER PUBLICATIONS

*Method in Molecular Biology*, Vol. 1, Proteins, Edited by John M. Walker, SDS Polyacrylamide Gel Electrophoresis of Proteins, Author–B.J. Smith pp. 41–54 (Humana Press––Clifton New Jersey).

Cleavage of Structural Proteins during the Assembly of the Head of Bacteriophage T4 by U.K. Laemmli; Nature Vo. 227, Aug. 15, 1970.

*Primary Examiner*—Tae Yoon
*Attorney, Agent, or Firm*—Marger Johnson McCollom & Stolowitz, P.C.

[57] ABSTRACT

A dehydrated reconstitutable polyacrylamide material for use as a polyacrylamide gel sample in electrophoretic analysis is provided. The dehydrated reconstitutable material includes a stabilizer material and excludes a buffer salt. The dehydrated reconstitutable polyacrylamide material is storable at ambient temperature without substantial loss of potency for at least about 120 days.

20 Claims, No Drawings

RECONSTITUTABLE POLYACRYLAMIDE MATERIALS AND METHODS FOR PRODUCING SAME

RELATED APPLICATION

This is a continuation of U.S. application No. 08/267,147, filed Jun. 24, 1994, now abandoned.

BACKGROUND OF THE INVENTION

This invention relates to polyacrylamide gels and methods for producing same for electrophoretic analysis, and more particularly to reconstitutable polyacrylamide materials which can be readily stored and then subsequently formed into polyacrylamide gel samples, as required, for use in electrophoretic analysis.

Polyacrylamide gel electrophoresis (PAGE) is a powerful technique commonly used in biochemistry and biomedicine research. Depending on the purpose, this technique can be used to perform either analytical or preparative studies of protein and nucleic acid. A book (article) entitled "SDS Polyacrylamide Gel Electrophoresis of Proteins" by B. J. Smith, relates to PAGE. The following are some of the common applications of PAGE which are used in protein chemistry and molecular biology:

1. Protein molecular weight determination.
2. Monitoring protein purification.
3. Preparative protein isolation.
4. Nucleic acid separation.
5. DNA sequencing.

PAGE was first introduced to the field of protein analysis more than twenty years ago. The most widely used PAGE procedure is that of Laemmli (1970). Electrophoretic separation of biological molecules on polyacrylamide gel is based on the net charge, shape and size of these molecules. These gels are typically formed by the polymerization of an acrylamide monomer solution. The process is initiated by adding a free radical-generating compound into the acrylamide solution. Gels are made with different concentration of acrylamide and cross linked by adding initiator (such as ammonium persulfate) and an accelerator, for example, tetramethyl-ethylenediamine (TEMED). A detergent, such as sodium dodecyl sulfate (SDS), or urea are incorporated into the gel if samples are analyzed under dissociation conditions.

Probably the most widely used of techniques for analyzing mixtures of proteins is SDS polyacrylamide gel electrophoresis. In this technique, proteins are reacted with the anionic detergent SDS, or sodium lauryl sulfate, to form negatively charged complexes. The amount of SDS bound by a protein, and so the charge on the complex, is roughly proportional to its size. Commonly, about 1.4 g. SDS is bound per 1 g. protein, although there are exceptions to this rule. The proteins are generally denatured and solubilized by their binding of SDS, and the complex forms a prolate ellipsoid or rod of a length roughly proportionate to the protein's molecular weight. Thus, proteins of either acidic or basic form negatively charged complexes that can be separated on the bases of difference in sizes by electrophoresis through a sieve-like matrix of polyacrylamide gel.

SDS-polyacrylamide gel electrophoresis is reproducible, versatile, and convenient. It uses either a tubular disc gel or a slab gel. The slab gel technique is an improvement of the disc gel electrophoresis. Less gel and sample materials are required per assay on a slab gel system, and the resulting gel can be easily used for further analysis. Electrophoresis on slab gel of full size (~16–20×16 cm), or mini-size (~10×10 cm) of 1.5 mm, 1.0 mm, 0.75 mm and even 0.5 mm thickness, is made with composition described by Davis (1964) and by Laemmli. The gel is typically prepared at an acrylamide concentration of 15%, 12%, 10%, 8% or 7.5% or of a gradient in concentration ranging from 5% to 20%. Often, a 4% stacking gel is casted on the top portion of the gel to facilitate good separations.

The conventional method to make slab polyacrylamide gel is by casting a polymeric gel between a pair of glass plates. Thus, the initiator-containing acrylamide gel solution is cast in the rectangular cavity formed between the two glass plates. The thickness of the gel is determined by the thickness of spacers inserted between the glass plates which form the cavity therebetween.

The acrylamide gel solution with TEMED added is poured into the space between glass plates. The gel forms after the acrylamide polymerization is completed. The bottom spacer portion is then removed from the assembly. To carry out electrophoresis, the lower part of the gel sits in a buffer bath and the top part of the gel is enclosed by a top buffer bath. Then, electrical current is applied to the system to separate molecules of protein or nucleic acid.

The chemical composition of the gel varies depending on specificity of experiments. Polyacrylamide gel electrophoresis is divided into denatured, partially denatured and non-denatured PAGE categories. Denatured PAGE system is used for protein and nucleic acid studies. For protein molecular weight determinations, the gel and the electrophoresis buffer include a detergent (SDS). In this way, the intra-molecular disulfide bonds of sample proteins are reduced before electrophoresis. In protein chemistry, PAGE in the presence of detergent SDS separates mixture of protein based on the molecular weight. During separation, while applying electrical current, diffusion through gel is minimized. Molecules resolve into narrow bands depend on their mobility in the gel matrix. Protein bands are visualized after staining. The gel is dehydrated for preservation or to continue with other analysis.

The denatured PAGE system is also used in nucleic acid and gene sequencing studies. The sequencing gel contains urea and/or foramide. After electrophoresis separation, radioactive labeled nucleotides are examined under UV light. The gel is also exposed to X-ray film for establishing a permanent record.

A partially denatured PAGE system uses a detergent-containing gel and buffer to assay non-denatured, native proteins. For non-denatured PAGE systems, neither gel nor buffer contains detergent. This is used to assay native proteins.

Most laboratories follow the conventional method for making their own gel (as previously described). All stock solutions except 10% ammonium persulfate are prepared and stored for one to six months. Powdered chemicals, such as acrylamide, bis-acrylamide, Tris base, HCl, SDS, ammonium persulfate, TEMED, urea, EDTA, boric acid and foramide, are available commercially for gel-making.

To make the gels described above in conventional way, laboratory personnel have to prepare several stock solutions. Several chemicals used in gel preparation are hazardous and require special cautions during handling. All chemicals used in gel mixture have to be at the highest purity, otherwise, aberrant electrophoresis results may occur. Furthermore, stock solutions take up space from cold storage facility such as refrigerator. On the day of preparing gels, the following procedure takes place:

1). A 10% ammonium persulfate solution is prepared.

2). Precise volumes of five stock solutions are measured out.

3). The solution is mixed and then deaerated under vacuum or aspirator.

Several commercial products such as pre-mixed acrylamide powders, pre-mixed acrylamide solutions, and pre-cast mini-gels are designed to simplify the gel making process. However, there are certain drawbacks related to each of the above mentioned products. Premixed powders do not eliminate the potential danger of handling bio-hazardous chemicals. Premixed acrylamide solutions at specific gel strength limit the application of electrophoresis and do not completely eliminate the materials handling problem. Limited shelf life of premixed solution means unavoidable wastes. In any case, the 10% ammonium persulfate solution has to be made the day of casting the gel. Pre-cast mini-gel provides convenience for electrophoresis at high cost with a short shelf life and requirement of special cold storage.

Consequently, a need exists for method of preparing polyacrylamide gel samples for electrophoresis analysis which reduces or eliminates the potential danger of handling bio-hazardous chemicals and which relieves the problem of cold storage space.

SUMMARY OF THE INVENTION

The method and system of the present invention overcomes all of the existing needs described above and provides for the formation of a polyacrylamide gel sample with desirable and advantageous properties employing a process which provides the requisite levels of simplicity, reduced cost, and fewer processing steps.

The advantages of the above-described method system for producing a polyacrylamide gel is as follows:

1. A dehydrated reconstitutable material can be prepared in quantities and stored for later use.

2. A dehydrated reconstitutable material can be regenerated in a buffer system to form a regenerated gel.

3. The gel is ready for electrophoresis in about 25 minutes.

4. The polyacrylamide material can be readily regenerated.

5. The regenerated gel of this invention is similar when employed in testing as a freshly made gel and produces comparable electrophoresis resolution of macromolecules.

6. After electrophoresis, the regenerated gel can be further processed or treated as a freshly prepared gel.

7. The subject method eliminates all the dealing with potentially bio-hazardous chemicals.

A dehydrated reconstitutable polyacrylamide material for use as a polyacrylamide gel sample in electrophoretic analysis is provided. The dehydrated reconstitutable polyacrylamide material comprises a polyacrylamide and a stabilizer material, but excludes a buffering salt. The total solids of the dehydrated reconstitutable polyacrylamide material can be from about 5 up to about 40 weight %, preferably 10 up to about 35 weight %, more preferably 12 up to about 32 weight %, and most preferably from about 15 up to about 30 weight %, based on the total weight of the dehydrated reconstitutable polyacrylamide material.

The stabilizer material preferably comprises glycerol or sucrose. The amount of said stabilizer material preferably comprises from about 1% up to about 40%, and more preferably from about 2% up to about 30% by weight, and most preferably from about 5% up to about 20% by weight, based on the weight of the acrylamide gel solution. The gel regenerating solution can also include a buffer salt, with or without a denaturing agent. It can also include a detergent and/or a denaturing agent.

The method of the present invention can include the further step of storing the dehydrated reconstitutable polyacrylamide material at ambient temperature for future use. This overcomes the need for cold storage.

Moreover, the subject method can include the further steps of providing a gel regenerating solution for regenerating the dehydrated reconstitutable polyacrylamide material, introducing the dehydrated reconstitutable polyacrylamide material into the gel regenerating solution; and regenerating the polyacrylamide gel sample for use in electrophoretic analysis. Preferably, the method of this invention can include the further steps of, after forming a gel regenerating solution for regenerating the dehydrated reconstitutable polyacrylamide material, providing a gel formation system, introducing the dehydrated reconstitutable polyacrylamide material into the interior of the gel formation system, introducing the gel formation system and the dehydrated reconstitutable polyacrylamide material into the gel regenerating solution, and regenerating the dehydrated reconstitutable polyacrylamide material for use in electrophoretic analysis.

DETAILED DESCRIPTION OF A PREFERRED EMBODIMENT

This invention relates to a method and system for producing a dehydrated reconstitutable polyacrylamide material which can be formed into a polyacrylamide gel sample typically for use in electrophoretic analysis. A plurality of chemical materials as previously described are employed for producing a polyacrylamide gel used to make the dehydrated reconstitutable polyacrylamide material. Preferably, the gel formation techniques of co-pending patent application U.S. Ser. No. 08/209,632, now U.S. Pat. No. 5,543,097, which is invented by same inventor as in the present patent application, and which is incorporated herein by reference, are employed to initially prepare the polyacrylamide gel. These include the use of a gel formation container which comprises a mixing bottle and a cap assembly including a compartment for storing pre-mixed ingredients for producing the polyacrylamide gel solution. It also includes an acrylamide gel sample formation system comprising a leak-proof formation chamber including a pair of plates and a unitary U-shaped spacer member.

The chemical materials conventionally specified for producing an acrylamide gel solution are employed as the chemical formulation for producing the subject dehydrated reconstitutable polyacrylamide material. The subject chemical formulation typically excludes a buffer salt but includes a stabilizer material. The purpose of the stabilizer material is to maintain the crosslinking of the acrylamide and to retain the shape of the polyacrylamide gel during dehydration. The stabilizer material typically comprises a material such as glycerol or sucrose. Preferably, the stabilizer material comprises from about 1% up to about 40% by weight, and more preferably from about 2% up to about 30% by weight, and most preferably about 5% up to about 20% by weight, of the total weight of the acrylamide gel solution.

Means defining a substantially leak-proof formation chamber can be provided for casting the polyacrylamide gel in sample form from the acrylamide gel solution. The leak-proof formation chamber generally comprises a pair of plates each having a pair of major surfaces and a easily-alignable spacer member. The plates are assembled so that a major surface of each plate is adjacent to the other plate with the spacer member located between the plates thereby defining the formation chamber for casting polyacrylamide gel samples.

Next, the acrylamide gel solution is introduced into the formation chamber. The polyacrylamide gel sample is formed in the formation chamber in an intact condition. The gel is then either preserved in between cellophane membranes or laid on a screen and then dehydrated using air for 24 hours.

The reconstitutable polyacrylamide material in dehydrated form can be stored at ambient temperature for subsequent regeneration and use in, for example, electrophoretic analysis. More specifically, the dehydrated reconstitutable polyacrylamide material is typically storable at ambient temperature without loss of potency for at least about 120 days, preferably at least about 180 days, and more preferably at least about 300 days, and most preferably at least about 450 days.

The regeneration step can be preferably attained by providing a gel solution for regenerating the dehydrated reconstitutable polyacrylamide material. Then, this is accomplished by introducing the dehydrated reconstitutable polyacrylamide material into the gel solution and thereby regenerating the polyacrylamide gel sample for use in electrophoretic analysis. The gel regenerating solution further preferably comprises a buffer salt, with or without a detergent.

In a preferred embodiment of this invention, a gel solution for regenerating the dehydrated reconstitutable polyacrylamide material is first formed. Two pieces of fine mesh screen to be used as the gel formation system are employed for implementing gel regeneration.

During regeneration, the dehydrated material is placed in a shallow dish or the like which is filled with a gel regenerating solution. After several minutes, the polyacrylamide will separate from the cellophane membrane, if present. The first mesh screen is then placed on the bottom of the dish. The polyacrylamide material is placed on top of the first mesh screen and is then covered with the second mesh screen. The dish is shaken slowly on a rotary shaker. A 12% polyacrylamide gel sample is fully regenerated after 25 minutes.

While the polyacrylamide gel sample is being regenerated, the glass plate assembly is being prepared. First, the glass plates are cleaned. The first plate, which typically is a large plate, is placed on the bench and a U-shaped spacer member is arranged on the top of the plate. Preferably, a PAGEMATE™ U-shaped spacer manufactured by Essex Research of Portland, Oreg., is employed for this purpose. The U-shaped spacer member comprises a horizontally-extending lower section and a pair of vertically-extending side sections of the U-shaped spacer member. Typically, the fully regenerated gel is placed on the large plate, aligned with the inner dimension of the U-shaped spacer. Excess gel is then trimmed off the sides. Next, the second glass plate, which is typically smaller in size, is placed on top of the U-shaped spacer member and the bottom of the glass plate assembly is clamped in position. The gel-glass plate assembly is then clamped onto an electrophoresis apparatus. Finally, the hold tab of the U-spacer is pulled to remove the bottom section and then the electrophoretic analysis is conducted in the usual manner.

The dehydrated reconstitutable material of the present invention can be formed from polyacrylamide gels produced as described in co-pending U.S. patent application Ser. No. 08/209,632, as follows:

(A) INITIAL GEL FORMATION. A polyacrylamide gel formulation typically comprises an acrylamide monomer solution (acrylamide and bis-acrylamide) of an appropriate strength, ammonium persulfate and TEMED. The gel mixture additionally contains a stabilizer material, typically glycerol or sucrose, but no buffer salt.

(B) GEL CASTING. A substantially leak-proof formation chamber system is typically employed for casting polyacrylamide gel samples. The system includes a easily-alignable, unitary, substantially U-shaped spacer member and a pair of plates, which are generally made of glass. The spacer member is formed from either silicon or plastic materials of different thickness. The spacer member includes pull tabs for use in the subsequent removal of its bottom section after gel formation is completed. The gel is casted according a predetermined size and thickness. After the polyacrylamide gel solidifies completely, the polyacrylamide gel formation assembly is taken apart and the gel is dehydrated in between cellophane membrane sheets so that it can be maintained in a pliable state. Alternatively, the gel is laid on a screen and is dehydrated in air.

(C) DEHYDRATED RECONSTITUTABLE MATERIAL FORMATION. Cellophane sheets are cut to the size bigger than the gel on all dimensions. Two sheets are needed for each polyacrylamide gel sample. The sheets are wetted briefly in a dish containing a solution of stabilizer material. One sheet is laid over a glass plate. The polyacrylamide gel is placed onto the sheet and it is then covered immediately with another sheet of cellophane. The excess cellophane is folded around the glass plate and clamped in place. This assembly is dehydrated using air overnight or under a fan in a shorter period of time. The dehydrated reconstitutable polyacrylamide material remains at its original dimensions together with cellophane sheet can be kept at room temperature for extended time and retain its potency. The gel dehydrated on a screen shrinks to approximately ⅓ of the original size. It is then stored in between a pair of cellophane or plastic sheet covers.

(D) GEL REGENERATION. To regenerate the dehydrated reconstitutable polyacrylamide material, the dehydrated reconstitutable polyacrylamide material together with the cellophane sheets is soaked in a gel regeneration solution. The gel regeneration solution can comprise the user's choice of different buffer salts with or without a detergent such as SDS. A preferred gel regeneration solution contains 0.375M Tris.HCl (pH 8.8) and 0.1% SDS. Within minutes, the cellophane sheets are separated from the polyacrylamide material and are removed from the buffer bath.

Using a gel formation system such a gel holder will facilitate regeneration and handling of the gel in the gel regeneration solution. When the gel swells to size, it can then be taken out of the bath, re-assembled within the glass plates and then, onto electrophoresis apparatus. Employing a spacer member, preferably a U-shaped spacer member, facilitates the re-assembly process.

The system is now ready for electrophoresis.

EXAMPLE 1

This example shows a method of making a dehydrated reconstitutable polyacrylamide material sample, and a regenerated polyacrylamide gel sample produced therefrom.

Polyacrylamide gel samples were initially produced using a formation procedure, as follows:

The gel were first prepared with the following stock solutions:

A. Acrylamide/Bis 30% T, total monomers; 2.67% C. % of cross-linking co-monomer in total monomer
B. 10% ammonium persulfate
C. 50% Glycerol
D. TEMED Working Solutions for preparing mini-size gels of different gel strength:

| Stock Solutions | 15% | 12% | 10% | 7.5% | 5% |
| --- | --- | --- | --- | --- | --- |
| Dist. Water | 2.45 | 3.45 | 4.12 | 4.95 | 5.78 |
| Soln. A, ml | 5.0 | 4.0 | 3.33 | 2.5 | 1.67 |
| Soln. B, µl | 50 | 50 | 50 | 50 | 50 |
| Soln. C, ml | 2.5 | 2.5 | 2.5 | 2.5 | 2.5 |
| Soln. D, µl | 5 | 5 | 5 | 5 | 5 |

Gel mixtures were prepared by mixing the above listed stock solutions in descending order except solution D. Mixture was deaerated for at least 15 minutes. Glycerol is added to the acrylamide before deaeration to an amount equal to 12.5% in weight. Solution D was added and mixed before by pouring mixture into the space in between glass plate-spacer member assembly where it is cast as a gel. A polyacrylamide gel sample measuring 10×10×0.1 cm was produced thereby.

The dehydrated reconstitutable material of this invention was formed according to the following procedure:

Cellophane sheets were cut to a size of 12×12 cm. Two sheets were needed for each polyacrylamide gel sample. The sheets were wetted briefly in a dish containing a solution of 12.5% glycerol. One sheet was laid over a glass plate. The polyacrylamide gel was placed onto the cellophane sheet and it is then covered immediately with another sheet of cellophane. The excess cellophane is folded to the back around the glass plate and clamped in place. This assembly was dehydrated for 24 hours with air to form a dehydrated reconstitutable product. The dehydrated reconstitutable material together with the cellophane sheet was kept at room temperature for a period of at least about 450 days.

Alternatively, the gel is laid on a screen to dehydrate same. The gel shrinks to about ⅓ the original size and can be stored away in between protective plastic or paper sheets. To regenerate the dehydrated reconstitutable polyacrylamide material, the dehydrated reconstitutable polyacrylamide material and the cellophane sheets or the shrunk dehydrated reconstituted material were soaked in a gel regenerating solution. The gel regenerating solution equilibrates and penetrates into the gel comprised buffer salts and SDS detergent. A preferred gel regenerating solution contains 0.375M Tris.HCl (pH 8.8) and 0.1% SDS. Within minutes, the cellophane sheets, if present, were separated from the polyacrylamide material and were removed from the buffer bath.

A gel formation system including a gel holder was employed to facilitate regeneration and reswelling of the gel in the gel regenerating buffer. The gel holder was porous. When the gel swelled to size, it was taken out of the bath, trimmed to size, re-assembled within the glass plates and then introduced onto electrophoresis apparatus. A U-shaped spacer member was employed to facilitate the re-assembly process.

The system was now ready for electrophoresis. The outcome of electrophoresis was comparable to freshly prepared gel. Furthermore the presence of glycerol in the polyacrylamide gel formulation did not affect the separation of protein bands during electrophoresis.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

I claim:

1. A method for producing a dehydrated reconstitutable polyacrylamide material, for use as a polyacrylamide gel sample in electrophoretic analysis, comprising providing an acrylamide gel solution consisting essentially of a solution of an acrylamide monomer, a cross-linking agent, water and a predetermined amount of a stabilizer material, and excluding a buffer salt;

forming a polyacrylamide gel sample from said acrylamide gel solution, including said predetermined amount of said stabilizer material, in an intact condition, for use in electrophoretic analysis; and dehydrating the polyacrylamide gel sample and thereby forming the dehydrated reconstitutable polyacrylamide material.

2. The method of claim 1, wherein the stabilizer material comprises glycerol or sucrose.

3. The method of claim 1, wherein said polyacrylamide gel sample formation step is conducted without the use of any additional stabilizer material.

4. The method of claim 1, which includes the further steps of providing a solution for regenerating the dehydrated reconstitutable polyacrylamide material; introducing the dehydrated reconstitutable polyacrylamide material into a gel regenerating solution; and regenerating the dehydrated reconstitutable polyacrylamide material to form a polyacrylamide gel sample for use in electrophoretic analysis.

5. The method of claim 4, wherein the gel regenerating solution comprises a buffer salt.

6. The method of claim 5, wherein the gel regenerating solution further comprises a denaturing agent.

7. The method of claim 1, which includes the further steps of providing a gel regenerating solution for regenerating the dehydrated reconstitutable polyacrylamide material; providing a gel formation system; introducing the dehydrated reconstitutable polyacrylamide material into the gel formation system; introducing the gel formation system including the dehydrated reconstitutable polyacrylamide material into the gel regenerating solution; and regenerating the polyacrylamide gel sample for use in electrophoretic analysis.

8. The method of claim 1, wherein the acrylamide gel solution consists essentially of acrylamide monomer, a cross-linking agent, water, an initiator, an accelerator and a stabilizer.

9. The method of claim 1, the dehydrated, reconstitutable polyacrylamide material is storable at ambient temperature without substantial loss of potency for at least about 120 days.

10. The method of claim 8, the dehydrated, reconstitutable polyacrylamide material is storable at ambient temperature without substantial loss of potency for at least about 120 days.

11. A method for producing a dehydrated reconstitutable polyacrylamide material for use as a polyacrylamide gel sample in electrophoretic analysis, comprising providing an acrylamide gel solution which consists essentially of an acrylamide monomer, a cross-linking co-monomer, water, an initiator, an accelerator and a stabilizer;

providing a formation chamber for casting polyacrylamide gel samples;

introducing the acrylamide gel solution into the formation chamber;

forming the polyacrylamide gel sample in the formation chamber in an intact condition for use in electrophoretic analysis; and dehydrating the polyacrylamide gel sample and thereby forming a dehydrated reconstitutable polyacrylamide material which is storable at ambient temperature without any loss of potency for at least about 120 days.

12. The method of claim 11, wherein the stabilizer material comprises glycerol or sucrose.

13. The method of claim 11, wherein said polyacrylamide gel sample formation step is conducted without the use of any additional stabilizer material.

14. The method of claim 11, which includes the further steps of providing a solution for regenerating the dehydrated reconstitutable polyacrylamide material; introducing the dehydrated reconstitutable polyacrylamide material into a gel regenerating solution; and regenerating the dehydrated reconstitutable polyacrylamide material to form a polyacrylamide gel sample for use in electrophoretic analysis.

15. The method of claim 14, wherein the gel regenerating solution comprises a buffer salt.

16. The method of claim 15, wherein the gel regenerating solution further comprises a denaturing agent.

17. The method of claim 11, which includes the further steps of providing a gel regenerating solution for regenerating the dehydrated reconstitutable polyacrylamide material; providing a gel formation system; introducing the dehydrated reconstitutable polyacrylamide material into the gel formation system; introducing the gel formation system including the dehydrated reconstitutable polyacrylamide material into the gel regenerating solution; and regenerating the polyacrylamide gel sample for use in electrophoretic analysis.

18. The method of claim 11, wherein the acrylamide gel solution consists essentially of acrylamide monomer, a cross-linking agent, water, an initiator, an accelerator and a stabilizer.

19. The method of claim 11, the dehydrated, reconstitutable polyacrylamide material is storable at ambient temperature without substantial loss of potency for at least about 120 days.

20. The method of claim 13, the dehydrated, reconstitutable polyacrylamide material is storable at ambient temperature without substantial loss of potency for at least about 120 days.

* * * * *